United States Patent [19]
Roques et al.

[11] Patent Number: 6,096,926
[45] Date of Patent: Aug. 1, 2000

[54] PERFLUOROALKYLATION METHOD AND REAGENT THEREFOR

[75] Inventors: Nicolas Roques, Lyons; James Russel, Rousson, both of France

[73] Assignee: Rhodia Chimie, Courbevoie, France

[21] Appl. No.: 09/077,131

[22] PCT Filed: Nov. 22, 1996

[86] PCT No.: PCT/FR96/01854

§ 371 Date: Feb. 22, 1999

§ 102(e) Date: Feb. 22, 1999

[87] PCT Pub. No.: WO97/19038

PCT Pub. Date: May 29, 1997

[30] Foreign Application Priority Data

Nov. 23, 1995 [FR] France .................................... 95 13996
Nov. 15, 1996 [FR] France .................................... 96 14134

[51] Int. Cl.$^7$ .......................... C07C 215/00; C07C 23/00; C07C 19/08

[52] U.S. Cl. .......................... 564/355; 564/503; 570/124; 570/134

[58] Field of Search .................................... 564/355, 503; 570/124, 134

[56] References Cited

PUBLICATIONS

CA: 126 : 72214 abstract of JP 08311036, Nov. 1996.

*Primary Examiner*—Paul J. Killos
*Assistant Examiner*—J. Parsa
*Attorney, Agent, or Firm*—Jean-Louis Seugnet

[57] ABSTRACT

The subject-matter of the present invention is a process of use in perfluoroalkylation and a reactant for making use of this process. This process is defined in that it comprises a stage in which a material of formula RfH and a base (or a species capable of generating a base) are brought into contact, in a polar and anhydrous medium, with a substrate carrying at least one electrophilic functional group. Application to organic synthesis.

2 Claims, No Drawings

PERFLUOROALKYLATION METHOD AND REAGENT THEREFOR

The subject-matter of the present invention is a process of use in perfluoroalkylation and a reactant for making use of this process. The invention more particularly relates to a reactant and a process for grafting a substituted difluoromethyl group onto a compound containing at least one electrophilic functional group. It more particularly relates to a technique for perfluoroalkylating different compounds by addition or nucleophilic substitution reactions typically carried out with organometallic derivatives.

Perfluoroalkylation techniques, or equivalent techniques, generally use derivatives of the perfluoroalkyl iodide type, in the presence of zinc. This technique is thus expensive, while requiring plants for the treatment of the metal wastes which it is advisable to treat, as zinc is a significant pollutant of water courses.

Other techniques, where the perfluoroalkyl radical does not form a stabilized reactive intermediate of the organometallic type, are generally difficult to employ because of the very low stability of the free perfluoro anions in the reaction mixtures. The latter generally result in products of the carbene type, which, when they react, have lost one of their substituents.

This is why one of the aims of the present invention is to provide a reactant which makes possible perfluoroalkylation according to a mechanism of the type involving a carbanion, without resorting to organometallic derivatives of transition metals, such as zinc.

Attempts have often been made to use perfluorocarboxylic acids as source of perfluoroalkyl radicals, more generally of trifluoromethyl radicals, by employing decomposition reactions targeted at removing the carboxyl fragment from the said acids with release of carbon dioxide. However, the successes which had been achieved were very mixed and used particularly complicated catalytic systems. The perfluoroalkyl radicals or their equivalents generated by the decomposition of the said perfluorocarboxylic acids were, in addition, unstable in the reaction mixture and required the use of stabilizing agents.

More recently, Shono, in an article entitled "A Novel Trifluoromethylation of Aldehydes and Ketones Promoted by an Electrogenerated Base" and published in J. Org. Chem., 1991, 56, 2–4, attempted to carry out perfluoromethylation reactions from fluoroform and showed that it was very difficult to obtain positive results in the absence of the base, composed of the pyrrolidonyl anion in combination with a quaternary ammonium cation, this being under the express condition that this base was generated by electrolysis.

During this comparative study, taking, as test reaction, the trifluoromethylation of benzaldehyde according to the so-called Barbier technique (which will be given in detail hereinbelow), this writer concluded that the results obtained from other bases gave zero or poor yields and that the side reactions, and in particular the Cannizzaro reaction (disproportionation of benzaldehyde to benzoic acid and benzyl alcohol), predominated [but the procedures relating to the usual bases (potassium tert-butoxide, sodium hydride, and the like) are not described therein].

However, the techniques using the electrogenerated bases described by this writer require, on the one hand, complex equipment and, on the other hand, a dexterity such that they are problematic to reproduce and extremely difficult to extrapolate to industrial scales. Finally, the use of quaternary ammonium compounds, which are very hygroscopic, implies great care.

The present invention provides a remedy for the disadvantages of the existing processes by providing a reactant which is non-toxic to the environment and which is capable of resulting in the desired products with a satisfactory yield. These aims and others which will appear subsequently are achieved by means of a process which comprises a stage in which a material of formula RfH and a base (or a species capable of generating a strong base in the presence of a compound containing mobile hydrogen, such as, for example, toluene; mention may be made, as example of such a species, of alkali metals or even alkaline earth metals) are brought into contact, in a polar and non-protic or only slightly protic medium, with a substrate carrying at least one electrophilic functional group, provided that, when the substrate is base-sensitive, the addition of the substrate is not carried out last, ♦ either by carrying out the addition, then optionally continuing the reaction after the addition, so that, on the one hand, at least 90% of the addition of the final component is carried out and that, on the other hand, the reaction mixture has been maintained for at least ½ hour (including the duration of the addition) at a temperature at most equal to −20° C., advantageously to −30° C.;

♦ or by meeting at least one of the, preferably both, conditions hereinbelow:
  ⇒ the water content is limited to a value at most equal to 200 ppm (two significant figures), advantageously to 100 ppm (two significant figures), preferably to 50 ppm (one significant figure);
  ⇒ or the amount of base is at most equal to 1.3 times the stoichiometric amount with respect to the substrate with a temperature at most equal to 0° C. or else the base is at most equal to 1.1 times the stoichiometric amount with a temperature at most equal to 20° C.

It should be pointed out that the above conditions are favourable even when the substrate is not base-sensitive. However, it can sometimes be advantageous to carry out reactions by departing somewhat from the optimum conditions when the economic conditions are it.

(cf. the preferred ranges of anhydrousness).

In the present description, H-Rf is understood to mean radicals of formula:

$$H-(CX_2)_p-EWG \qquad (II)$$

where the X, which are alike or different, represent a fluorine or a radical of formula $C_nF_{2n+1}$ with n an integer at most equal to 5, preferably to 2, or a chlorine;

where p represents an integer at least equal to 1 and at most equal to 2;

where EWG represents an electron-withdrawing group, the possible functional groups of which are inert under the reaction conditions, advantageously fluorine or a perfluoro residue of formula $C_nF_{2n+1}$ with n an integer at most equal to 8, advantageously to 5;

with the condition that X can only be chlorine once on the same carbon. The case where the carbon carrying the hydrogen atom exhibits two X other than chlorine is particularly advantageous.

It is also desirable that, among the X and EWG, at least one, advantageously 2, are atoms (of chlorine or of fluorine).

The total carbon number of Rf is advantageously between 1 and 15, preferably between 1 and 10.

In the material RfH of the reactant of the invention, the EWG entity which exerts an electron-withdrawing effect on the difluoro carbon atom is preferably chosen from functional groups with a Hammett constant $\sigma_p$ at least equal to 0.1. In addition, it is preferable for the inductive component of $\sigma_p$, $\sigma_i$, to be at least equal to 0.2, advantageously to 0.3. In this respect, reference will be made to the work by March, "Advanced Organic Chemistry", third edition, John Wiley and Son, pages 242 to 250, and in particular to Table 4 in this section.

More particularly, the electron-withdrawing entity can be chosen from halogen atoms, preferably light halogen atoms [in particular chlorine and fluorine]. The corresponding material RfH is, when p is equal to 1, a haloform.

EWG can also be advantageously chosen from nitrile, carbonyl-containing, sulphonated and perfluoroalkyl-containing groups.

Preferred materials of formula RfH of this type which can be used correspond to the formula R—G—CF$_2$—H
- where G represents a divalent group of formula —Z—G'— in which
  ♦ the divalent Z represents a single bond, a chalcogen atom, or a divalent residue —Y(R')—, where R' is a hydrocarbon-comprising radical of at most ten atoms, advantageously of at most six atoms, advantageously of at most two atoms, of carbon and where Y is a semimetallic atom from column V (nitrogen, phosphorus, and the like);
  ♦ G' represents >C=O, >S=O, —SO$_2$— or —(CF$_2$)$_n$— with n an integer greater than or equal to 1;
- and where R represents, without distinction, an organic or inorganic residue, preferably an organic radical such as aryl or alkyl, including aralkyl, which is optionally substituted. R can also represent a solid inorganic or organic support, such as a resin;
- or else the R—G combination represents a nitrile, ester or amide group (advantageously not carrying hydrogen), including a sulphamide group.

In the case where G represents a perfluoro-alkylene group —(CF$_2$)$_n$—, n is advantageously between 1 and 10, preferably between 1 and 5. However, in this case, R can also represent a halogen atom, in particular fluorine.

Thus, according to an advantageous alternative form of the present invention, the said material of formula RfH corresponds to the formula II where EWG represents an electron-withdrawing group of formula III:

$$R—C_nX'_{2n}—\quad\quad\quad(III)$$

where n is an integer at most equal to 5,
where R is chosen from hydrogen, a hydrocarbon-comprising radical, such as aryls and alkyls containing 1 to 10 carbon atoms, and light halogens (chlorine or fluorine, advantageously fluorine);
where the X', which are alike or different, represent a light halogen (chlorine or fluorine, advantageously fluorine) or a radical of formula C$_m$F$_{2m+1}$ with m an integer at most equal to 5, preferably to 2.

When R represents a hydrogen, the reaction is more complex, it being possible for the said material to react by several ends; and the ratios of the reactants to one another must take into account this reactivity in the stoichiometry. This polyvalency of the materials can be a disadvantage and, for this reason, the value hydrogen for R is not generally desirable.

It is desirable for at least three quarters, advantageously at least nine tenths, preferably all, optionally less one, of the X and of the X' to be fluorines or perfluoroalkyls (stricto sensu, to be of general formula of type C$_v$F$_{2v+1}$).

The acid associated with the said base advantageously has a pK$_a$ at least equal to 15.

However, in order to obtain good results, it is necessary either for the said substrate carrying at least one electrophilic functional group to be very favourable (aldehyde or ketone not having acidic hydrogen at the alpha position) or for the acid associated with the said base to have a pK$_a$ at least equal to 20, advantageously to 25, preferably to 30.

In addition, especially when the base is in the low region of the above values, it is desirable for the said base to have an associated acid which is volatile under the reaction conditions.

Advantageously, the said polar and anhydrous medium is such that the strongest acid present in the medium, not taking into account the material RfH and the substrate, has a pK$_a$ at least equal to 25, advantageously to 30, preferably to 35.

The more aprotic the medium, that is to say the lower its content of protons which can be released into the reactant, the lower the risk of side reaction and the better the yield.

Thus, it is preferable, in the reactant, for the content of labile hydrogen atoms to be at most equal to ⅓, advantageously to ¼, preferably to 10% (in moles), with respect to the initial content of that of the said base or of the said material which is not in excess.

This effect is particularly important when the reaction is carried out at a temperature greater than approximately 240° K. (in the present description, the term "approximately" is employed to emphasize the fact that, when the figure or figures furthest to the right of a number are zeros, these zeros are positional zeros and not significant figures, unless, of course, it is otherwise specified).

The main impurity, carrying labile hydrogen atoms, is generally water, which is capable of releasing up to two hydrogen atoms per molecule.

For this reason, the said polar medium is advantageously anhydrous, including substrate and the material RfH, that is to say that it has a molar amount of water less than a third of the amount of base introduced, advantageously than a quarter, preferably than a tenth. This restriction on anhydrousness is not very important for processes where the reaction is carried out at temperatures of less than 240° K. (two significant figures).

Generally, it is preferable to use reactants and solvents which are carefully dehydrated, so that the content by weight of water in the reactant is at most equal to 1 per 100, advantageously 1 per 1000, preferably to 1 per 10,000, with respect to the total mass of the reactant.

Moreover, it could be shown that other elements, namely transition elements having two stable valency states, such as copper, might not be propitious, indeed could be harmful.

Although this reactant according to the invention does not require a catalyst, such metal elements can be present as impurities introduced in particular by the solvent.

Thus, it is preferable for the molar content of these elements to be less than 1000, advantageously than 100, preferably than 10, ppm with respect to the initial content of the said material RfH.

Equally, although the use, with perfluoroalkylation agents, of elements from column VIII of the periodic classification of the elements has frequently been recommended, in order to promote certain substrates and to promote certain types of reaction, this has not proved to be particularly propitious for the reaction targeted above. For this reason, it is preferable to use reactants not containing metals from column VIII, in particular metals from the platinum lode, which is the group composed of platinum, osmium, iridium, palladium, rhodium and ruthenium.

In the present description, reference is made to the supplement to the Bulletin de la Société Chimique de France, Number 1, January 1966, where a periodic classification of the elements was published.

Thus, it is preferable for the content of metals from the platinum lode, indeed of metals from column VIII, to be less than 100 ppm, advantageously than 10 ppm, preferably 1 ppm. These values apply with respect to the starting base and are expressed in moles.

More generally and more empirically, it may be indicated that these two categories of metals, namely transition elements with two valency states and elements from column VIII, should be present in the reactant at an overall concentration level at most equal to 1000 ppm on a molar basis, preferably to 10 ppm on a molar basis.

It will be noted that the different metals present at such an overall concentration level are in an extremely low amount and, in this respect, they play no catalytic role. Their presence does not improve the kinetics of the reaction, indeed is harmful to it when they are present in an excessively large amount.

The use, in addition to the abovementioned reactant components, of alkali metal fluoride or of quaternary phosphonium fluoride [indeed of quaternary ammonium fluoride, if the constraints which this type of compound engenders are observed], commonly present in the reactant systems using fluorinated carboxylates, has not proved to be harmful but it has generally proved to be of little advantage, in particular because of the fact that it produces saline effluents which are difficult to treat. For this reason, it is preferable to limit their content, in particular their initial content. Thus, it is preferable for the content of fluoride, which is described as ionic, that is to say capable of being ionized in the polarizing medium of the reactant, to be at most equal to the initial molar concentration of the said material RfH, advantageously to half, preferably to a quarter.

The said polar medium can contain solvents.

Even if it is a tautology, it should be recalled that the solvent (which can comprise several constituents) must be liquid at the temperatures of use.

It may in particular be indicated that it is desirable for the said solvent to have a starting freezing point (appearance of a solid phase resulting from the solvent) at most equal to 10° C., advantageously to 0° C., preferably to −10° C. In the case where it is desired to be able to operate with a greater tolerance of $H^+$ and/or of water (a case in particular where it would be desirable to use quaternary ammonium compounds), the choice is advised of a solvent with a starting freezing point (appearance of a solid phase resulting from the solvent) at most equal to −30° C.

Thus, the solvents themselves can be composed of mixtures. These mixtures can in particular contain polar solvents and solvents which are non-polar or only slightly polar, which will be described hereinbelow as diluent.

As was mentioned above, the solvent plays an important role in the present invention and must be aprotic and advantageously polar and contain very few impurities carrying acidic hydrogen.

It is thus preferable for the polar aprotic solvent which can be used to have a significant dipolar moment. Thus, its relative dielectric constant $\epsilon$ is advantageously at least equal to approximately 5. Preferably, $\epsilon$ is less than or equal to approximately 50 (in the present description, the term "approximately" is employed to emphasize the fact that, when the figure or figures furthest to the right of a number are zeros, these zeros are positional zeros and not significant figures, unless, of course, it is otherwise specified) and greater than or equal to 5.

In addition, it is preferable for the polar solvents of the invention to be capable of satisfactorily solvating the cations, which can be codified by the donor number D of these solvents. It is thus preferable for the donor number D of these solvents to be between 10 and 30, advantageously between 20 and 30. The said donor number corresponds to the $\Delta H$ (variation in Enthalpy), expressed in kilocalories, of the combination of the said polar aprotic solvent with antimony pentachloride. More specifically, the work by Christian Reichardt [Solvents and Solvent Effects in Organic Chemistry, VCH, p. 19 (1988)] gives the definition of the donor number, which is defined as the negative ($-\Delta H$) of the enthalpy (kcal/mol) of the interaction between the solvent and antimony pentachloride in a dilute dichloromethane solution.

One of the advantages of cryptands is to make it possible to be freed at least partially from solvents with a high donor number.

According to the present invention, it is preferable for the reactant not to have acidic hydrogen on the polar solvent or solvents which it contains. In particular, when the polar nature of the solvent or solvents is obtained by the presence of electron-withdrawing groups, it is desirable for there not to be hydrogen alpha to the electron-withdrawing functional group.

More generally, it is preferable for the $PK_a$ corresponding to the first acidity of the solvent to be at least equal to approximately 20 ("approximately" underlining that only the first figure is significant), advantageously at least equal to 25, preferably between 25 and 35.

It is preferable for the base to be at least partially, preferably completely, soluble in the medium constituting the reactant. It is the same with the material of formula RfH.

The polar solvents giving good results can be in particular solvents of the amide type. Amides also comprise amides with a specific nature, such as tetrasubstituted ureas and monosubstituted lactams. The amides are preferably substituted (disubstituted for ordinary amides). Mention may be made, for example, of pyrrolidone derivatives, such as N-methylpyrrolidone, or N,N-dimethylformamide or N,N-dimethylacetamide.

Another particularly advantageous category of polar solvents is composed of ethers, whether symmetrical or non-symmetrical, whether open or cyclic. The various derivatives of glycol ethers, such as the various glymes, for example diglyme, should be incorporated in the category of ethers. Another category may also be cited: sulphoxygenated derivatives, such as sulphoxides and in particular DMSO. Thus, the most appropriate polar solvents, because of their price and their properties, are advantageously chosen from ethers, in particular cyclic ethers, such as THF, or polyfunctional ethers, such as glymes, those of amides which, such as DMF or DAAUs (N,N'-DiAlkylAlkyleneUrea), such as DMEU (N,N'-DiMethylEthyleneUrea) or DMPU (N,N'-DiMethylPropyleneUrea), do not have acidic hydrogen, and heterocycles with a basic nature, such as pyridine, and their mixtures.

In addition to polar solvents proper, which play a solvation role which is correlated with the donor number, the solvent can comprise diluents which do not have this property. Mention may be made, among diluents, of aliphatic or aromatic hydrocarbons, such as alkanes or aryl derivatives. Mention should be made of arylmethanes which can both act as diluent (because they are inert under the reaction conditions) and as sources of base, when the latter is preprepared in situ.

The countercations capable of potentiating the base, in order to cause the material of formula RfH to react, are advantageously bulky. Thus, alkali metal salts, advantageously those in which the alkali metal is chosen from sodium, potassium, rubidium, cesium and francium, are preferred. The said metal is preferably from a period with a rank at least equal to that of sodium, advantageously to that of potassium. Preference is also given to quaternary phosphonium salts, indeed quaternary ammonium salts if the constraints which this type of compound engenders are observed.

It is also possible to improve the reaction, in particular when the solvent is ether or contains it, by using cations which are either naturally bulky, such as quaternary phosphoniums [indeed quaternary ammoniums, if the constraints which this type of compound engenders are observed], or rendered bulky by the addition of chelating agents or, preferably, cryptands, such as, for example, crown ethers or derivatives which contain both amine groups and oxygen atoms. Although they exhibit the disadvantage, often prohibitive, of being very hygroscopic, quaternary ammonium cations or cations with a quaternary ammonium functional group can be used, provided that drastic precautions are taken.

The said substrate can be chosen from halogenated or pseudohalogenated hydrocarbon-containing compounds, in particular alkyl, aryl or aralkyl halides or pseudohalides, halogenated derivatives of organic silicon compounds, in particular silane or siloxane halides, halogenated derivatives of organic sulphur compounds, in particular sulphenyl, sulphinyl or sulphonyl halides, where the halogen atom or the pseudohalogen group is substituted during the reaction by a substituted difluoromethyl group, or compounds of thiocyanate type where the cyano group is substituted during the reaction by a substituted difluoromethyl group. When the tetrahedral intermediate is present (Grignard technique in the presence of a carbonyl which can be added to in a stable way: amide) and where the substrate is such that the fluoroalkylation reaction cannot pass (or passes with difficulty) through an addition intermediate, this type of substrate can change, in particular give a stable derivative of the tetrahedral intermediate, that is to say that the Nucleophilic Substitution takes place via the tetrahedral derivative and not via the Rf$^-$.

In the above compounds, the halogen atom can be chosen from iodine, bromine, chlorine and fluorine atoms. A "pseudohalogen" group is a group which, starting in the anionic form, has an associated acid with a p$K_a$ of less than 4, preferably than 3, in particular than 0.

Preference is given to the groups for which the associated acid has an acidity (measured by the Hammett constant) at least equal to that of acetic acid, advantageously to that of sulphonic acids or of α-trihalogenated acids. One of the typical pseudohalogens is a perfluoroalkanesulphonyloxy group which releases a perfluoroalkanesulphonate. Preferred pseudohalogen groups can be chosen from groups which give a leaving group belonging to the sulphonates, the paradigms of which, because they are the most used, are tosylates (p-toluenesulphonyloxy anion or p-toluenesulphonyloxylate), mesylate (methylsulphonyloxylate), triflate (trifluoromethylsulphonyloxylate) or else α-polyhalogenated carboxylates, one of the paradigms of which is trifluoroacetate. The acyloxylate group (that is to say carboxylate, for example acetate) can even be regarded as such a leaving group.

During the study which led to the present invention, it was, however, shown that it is desirable for the said substrate to carry at least one electrophilic functional group by addition. In other words, for the reaction to take place, at any rate as a transition reaction, by addition to a functional group exhibiting a double bond (naturally including that of donor-acceptor type) or a doublet belonging to a semimetallic with a period with a rank at least equal to 3.

Thus, according to a particularly advantageous implementation of the present invention, such an electrophilic functional group by addition is chosen from carbonyl or thiocarbonyl (>C=S) functional groups, optionally conjugated with one or more bonds of ethylene type, chalcogenides (in which the chalcogen has an atomic rank at least equal to that of sulphur) carrying a good leaving group (see above) and in particular dichalcogenides (in which the chalcogens have atomic ranks at least equal to that of sulphur).

Thus, the reactant also advantageously reacts with a compound chosen from carbonyl-containing compounds of ketone, aldehyde, activated ester (or acid halide) or non-activated ester type, an addition to the carbonyl functional group being carried out. The reaction product is an alcohol or alkoxide, in which the carbon atom carrying the hydroxyl functional group is substituted by a substituted difluoromethyl group. These transitory alkoxides, after hydrolysis (generally acidic hydrolysis), give the substitution or addition compound. The case of amides is expanded upon in the passage relating to the tetrahedral intermediate.

When there is a risk of the electrophilic functional group of the substrate giving reactions of transesterification type with the base, it is then desirable to choose one or both of the following measures, namely:

that the basicity of the leaving group is similar to or greater than that of the base initially employed as reactant, the route consisting in using the reactant of Grignard type.

In order to avoid certain side reactions, it is desirable for the said substrate not to be acidic or to have a P$K_a$ at least equal to 20, advantageously to 25, preferably to 30.

The overall carbon number of the substrate is not limited, other than by the solubility in the medium (advantageously at least equal to one tenth, preferably one, millimol per litre), and can reach approximately 50. However, it is preferable not to exceed approximately 30 carbon atoms.

The reaction is generally carried out at a temperature of between the melting temperature of the medium and the boiling temperature under the pressure conditions of the reaction.

More specifically, the reaction is carried out in the liquid phase, at a temperature of between approximately −100° C. and 160° C., advantageously between approximately −60° C. and 100° C. When RfH is very volatile, it is preferable to make sure that there is no evaporation; to do this, it is advisable either to prevent the difference between the reaction temperature and the boiling point being excessively large, more specifically it is desirable to operate at a temperature which is not greater than the boiling point (at atmospheric pressure) by plus 100° C. (two significant figures), advantageously by plus 80° C.; or to operate in a closed vessel, or to operate under a high partial pressure of the said RfH or to operate by the Grignard technique. It is possible and even advantageous to combine at least two of the above measures.

Finally, in the case of employing of Barbier type, even under very anhydrous conditions, the formation of carbene is promoted by the temperature. This formation of carbene is correlated with the release of hydrohalic acid, which promotes the side reactions. It is consequently preferable to avoid operating at temperatures at most equal to room temperature (20° C.) when there is such a risk (essentially when the carbon number of RfH is equal to 1 or when EWG and/or X is a chlorine).

When the substrate is sensitive to basic degradation, it is also preferable to operate at a temperature at most equal to room temperature. If there is a twofold risk of formation of carbene and sensitivity to the base of the substrate, it is then preferable not to exceed approximately 10° C. According to an advantageous alternative form of the present invention, the reaction is carried out so as to introduce firstly the substrate, then the material RfH and finally the base. This alternative form will be denoted hereinafter under the expression of Barbier alternative form [see "March", fourth edition, page 921 (ref. 365)].

According to particularly advantageous implementation of the present invention, the reaction is carried out so as to introduce firstly into the medium either the material RfH or the base and finally the substrate. In other words, to form a reactant from the material RfH, from the base and, if appropriate, from the solvent and/or from the diluent, and then to react this reactant with the substrate. This alternative form will be denoted hereinbelow under the expression of Grignard alternative form.

In the above two alternative forms, the reaction is carried out so as to introduce the final component of the reactant gradually and advantageously over a period of time of between 5 and 300 minutes.

The reaction is carried out so as to introduce the said base gradually and advantageously over a period of time of between 5 and 300 minutes. (cf. description of the reactant below).

In addition, it is desirable, in particular when the reaction is carried out at "high" temperatures (that is to say, at least equal to 240° K.), for the ratio of the amount of material RfH to the base (RfH/base) to be at least equal to 1, advantageously to 2, times and at most equal to 10; preferably at least equal to 1 three times the stoichiometric amount and at most equal to 5 times.

Especially and mainly if the reaction is being carried out according to the Barbier technique, when the substrate is sensitive to degradation by base, it is advisable to restrict the amount thereof and especially the excess; thus, in the case where the substrates are susceptible to disproportionation, as is the case with aldehydes which can give rise to Cannizzaro and/or Tishchenko reactions or crotonization reactions, it is advisable to limit the amount of base to 4/3, advantageously to 5/4, preferably to 1.1, the S.A. (that is to say, Stoichiometric Amount) with respect to the substrate.

The use of the so-called Grignard procedure, in particular in the presence of amide(s) (preferably those targeted as precursor of the tetrahedral compound, cf. below), essentially overcomes the problem and thus makes it possible to use large excesses of base and thus of reactant. An excess of 20 to 300% is then possible; however, it is preferable to limit it, for reasons of cost, generally to a value of approximately 100%. Of course, the same values are applicable when the substrate is sensitive to bases.

Another aim of the present invention is to provide a reactant which can be used for perfluoroalkylation.

This aim and others which will become apparent subsequently are achieved by means of a reactant containing a material of initial formula RfH and a base (or a species capable of generating a base) in a polar and anhydrous medium.

Advantageously, the reactant additionally contains at least one polar aprotic solvent.

In addition, it is desirable for the ratio of the amount of material RfH to the base (RfH/base) to be between 3 and ½ times the stoichiometric amount.

As has been mentioned above, the solvent plays an important role in the present invention and must be aprotic and advantageously polar and contain very few impurities carrying acidic hydrogen.

It is thus preferable for the polar aprotic solvent which can be used to have a significant dipolar moment. Thus, its relative dielectric constant $\epsilon$ is advantageously at least equal to approximately 5. Preferably, $\epsilon$ is less than or equal to 50 (the positional zeros are not regarded as significant figures in the present description unless it is otherwise specified) and greater than or equal to 5.

In addition, it is preferable for the solvents of the invention to be capable of satisfactorily solvating the cations, which can be codified by the donor number D of these solvents. It is thus preferable for the donor number D of these solvents to be between 10 and 30. The said donor number corresponds to the $\Delta H$ (variation in Enthalpy), expressed in kilocalories, of the combination of the said polar aprotic solvent with antimony pentachloride.

According to the present invention, it is preferable for the reactant not to have acidic hydrogen on the polar solvent or solvents which it uses. In particular, when the polar nature of the solvent or solvents is obtained by the presence of electron-withdrawing groups, it is desirable for there to be no hydrogen alpha to the electron-withdrawing functional group.

More generally, it is preferable for the $pK_a$ corresponding to the first acidity of the solvent to be at least equal to approximately 20 ("approximately" underlining that only the first figure is significant), advantageously at least equal to 25, preferably between 25 and 35.

It is preferable for the said acid or acid salt and the said material to be at least partially, preferably completely, soluble in the medium constituting the reactant.

The solvents giving good results can be in particular solvents of the amide type. Amides also comprise amides with a specific nature, such as tetrasubstituted ureas and monosubstituted lactams. The amides are preferably substituted (disubstituted for ordinary amides). Mention may be made, for example, of pyrrolidone derivatives, such as N-methylpyrrolidone, or N,N-dimethylformamide or N,N-dimethylacetamide.

Another particularly advantageous category of solvents is composed of ethers, whether symmetrical or non-symmetrical, whether open or not. The various derivatives of glycol ethers, such as the various glymes, for example diglyme, should be incorporated in the category of ethers.

Thus, the most appropriate solvents, because of their price and their properties, are advantageously chosen from ethers, in particular cyclic ethers, such as THF, or polyfunctional ethers, such as glymes, those of amides which, such as DMF or DAAUs (N,N'-DiAlkylAlkyleneUrea), such as DMEU (N,N'-DiMethylEthyleneUrea) or DMPU N,N'-DiMethylPropyleneUrea), do not have acidic hydrogen, and heterocycles with a basic nature, such as pyridine.

When they are employed, the amides used play a greater role than appears at first glance and they play a role in the formation of the reactant. This is because it has been possible to demonstrate that the reactant formed in the amides (especially when they correspond to the precursor of the formula of the tetrahedral compound hereinbelow) was a reactant in which the reactive species was the addition compound of $CF_3$- to the carbon of the carbonyl functional group, the oxygen of the latter functional group becoming anionic. It is this compound which acts as carrier of $CF_3^-$ or more specifically of $Rf^-$. An important characteristic of this novel reactant is consequently the presence of this species in the reactant. The present invention is consequently also targeted at reactants containing the compounds of formula (IV) $Rf—C[O^-(M^+)] [R_{13}] [N(R_{11}) (R_{12})]$

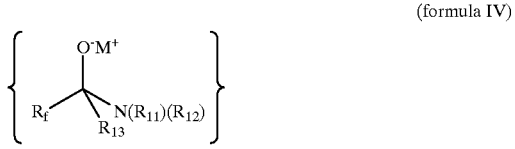

(formula IV)

Of course, the above formula is also targeted at the other enantiomer.

This intermediate can be identified by fluorine NMR (in the case of dimethylformamide, δ of approximately 1 ppm [doublet difficult to resolve] with respect to $HCF_3$). In this formula, $M^+$ represents an advantageously monovalent cation corresponding to the bases specified in the present description; advantageously alkali metals and phosphoniums.

Rf has already been defined above, and $R_{11}$, $R_{12}$ and $R_{13}$ represent hydrocarbon-comprising or aryl chains, including alkylaryl or alkyl chains, including aralkyl and cycloalkyl chains, it being possible for these chains to be connected to one another in order to form one (or more) ring(s). As regards $R_{13}$, $R_{13}$ has a Hammett constant value of less than 0.2 in absolute value, preferably than 0.1.

However, $R_{13}$ can also take the value hydrogen and this is its preferred value. Another value satisfying $R_{13}$ is the value aryl, the Hammett constant of which is advantageously less than 0.2 in absolute value, preferably than 0.1. This intermediate exhibits good stability, in particular at low temperatures (for example −10, advantageously −20, preferably −30° C.).

Thus the present invention is targeted at a reactant of the above type which contains at least one compound of formula IV at a concentration at least equal to one millimol per litre, advantageously to 5 millimol per litre, preferably 10 millimol per litre.

This intermediate can act as perfluoroalkylation reactant, as described above, but can also constitute a reaction intermediate resulting in advantageous compounds, in particular aldehyde, O-silylated derivative, (bi)sulphite derivative or O-acylated derivative.

When it is used as perfluoroalkylation reactant, it is preferable for the $R_{11}$, $R_{12}$ and $R_{13}$ groups to be small in size, that is to say for, when they are alkyls, their carbon number to be advantageously at most equal to 6, advantageously to 3, preferably methyls; when they are aryls, advantageously phenyls (substituted or unsubstituted), it is preferable for their carbon number advantageously to be at most equal to 10, advantageously to 8. It is preferable for the $R_{11}$, $R_{12}$ and $R_{13}$ groups to have, overall, a carbon number at most equal to 15, advantageously to 12, preferably to 8.

When it is not used as perfluoroalkylation reactant but as synthetic intermediate, the $R_{11}$, $R_{12}$ and $R_{13}$ groups can be greater in size (provided that it is soluble in the medium) and the overall carbon number can then reach approximately 50. However, it is preferable not to exceed approximately 30 carbon atoms.

It is therefore highly recommendable, on using the Grignard reactant, to use, alone or as a mixture (optionally with other amides), amides of formula $R_{13}—CO—N(R_{11}) (R_{12})$, the recommended ratio of these amides to the base used then being at least equal to 1, advantageously to 2, preferably to 5. There is no upper limit, except that it (they) constitute(s) all the polar solvent. When these amides are used as solvents more often than not in the tests carried out (without this necessarily being an optimum), the content of these amides with respect to the sum of the polar solvents is between approximately 40 and 80%.

Mention may be made, among the diluents, of aliphatic or aromatic hydrocarbons, such as alkanes or aryl derivatives. Mention should be made of arylmethanes which can both act as diluent (because they are inert under the reaction conditions) and as sources of base when the latter is prepepared in situ.

The following non-limiting examples illustrate the invention.

TYPICAL PROCEDURE: FLUOROFORM

"Barbier" Method

Fluoroform 0 is added by bubbling to a suitably stirred solution[*] of substrate in the anhydrous solvent at most equal to approximately 100 ppm (mass) maintained at −50° C. The bubbling into this solution is carried out over approximately 15 min. A base, generally in solution in a polar solvent, generally ether [cyclic or non-cyclic, such as THF, symmetrical or non-symmetrical dialkyl ether (for example, dimethyl ether, diethyl ether, dibutyl ethers, methyl ethyl ether, and the like), or polyether, such as glymes], is then added dropwise over 20 min, the temperature being maintained at −50° C.

[*]Handling under an inert argon atmosphere.

The reaction mixture is left without stirring at −50° C. for an additional 10 min.

An excess of acetic acid is added at this same temperature and the temperature is allowed to rise to room temperature.

"Grignard" Method

A base or a solution of base in a polar solvent, generally ether [cyclic or non-cyclic, such as THF, symmetrical or non-symmetrical dialkyl ether (for example, dimethyl ether, diethyl ether, dibutyl ethers, methyl ethyl ether, and the like), or polyether, such as glymes], is added dropwise at −40° C. and over a period of 10 min to a suitably stirred solution[*] of fluoroform in anhydrous DMF.

The reaction mixture is left without stirring for 30 min at −40° C., before adding the substrate.

This solution is kept without stirring at −40° C. for an additional 30 min, before the addition of acetic acid.

The temperature is allowed to rise to room temperature and the composition of the mixture is determined by GLC assaying with internal calibration.

EXAMPLE NO. 1

ROLE OF THE ORDER OF ADDITION OF THE REACTANTS

⇒ General procedure 1 (so-called "Barbier" method)

Fluoroform (4.9 g, 70 mmol) is added over a period of 15 minutes to a suitably stirred solution (400 r/min), maintained at −50° C., of benzaldehyde (0.64 g, 6 mmol) in anhydrous DMF. A 1M solution of t-BuOK in THF (5 ml, 5 mmol) is then added dropwise over 20 minutes, the temperature being maintained at −50° C.

The reaction mixture is left stirring at −50° C. for an additional 10 minutes, before addition of acetic acid (0.5 ml).

The composition of the mixture is determined by GLC assaying with internal calibration:

DC(PhCHO)=74%
RY(PhCHOHCF$_3$)=60%
RY(PhCH$_2$OH)=0.3%

It is noticed, and this is general throughout the Application, that, in particular for base-sensitive substrates, an amount of base of less than stoichiometry with respect to the substrate gives excellent results in the Barbier method.

⇒ General procedure 2 (so-called "Grignard" method)

A 1M solution of t-BuOK in THF (5 ml, 5 mmol) is added dropwise at −40° C. over a period of 10 minutes to a suitably stirred (400 r/min) solution of fluoroform (3.0 g, 43 mmol) in 30 ml of anhydrous DMF. The reaction mixture is left stirring for 30 minutes at −40° C., before adding benzaldehyde (0.47 g, 4.4 mmol).

The solution is left stirring at −40° C. for an additional 30 minutes, before addition of acetic acid (0.5 ml).

The composition of the mixture is determined by GLC assaying with internal calibration:

DC(PhCHO)=67%
RY(PhCHOHCF$_3$)=46%
RY(PhCH$_2$OH)⇒ traces

EXAMPLE NO. 2

ROLE OF THE SIDE REACTIONS (CANNIZZARO REACTION ACCORDING TO T. SHONO)

In the reaction between benzaldehyde and the CF$_3$H/t-BuOK/DMF system, if the operating conditions are not well chosen, side reactions (and in particular formation of benzyl alcohol attributed to the Cannizzaro reaction by T. Shono) predominate.

General procedure 1 (variation in the reaction temperature and in the number of equivalents of base employed).

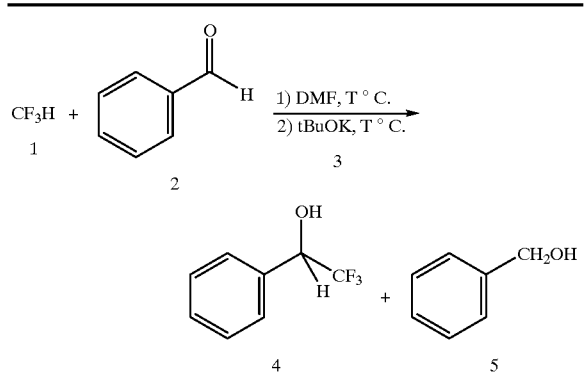

| Experimental Parameters | DC (2) % | YD (4) % | YD (5) % |
| --- | --- | --- | --- |
| Excess of base (2.2 eq) at −50° C. | 97 | 69 | — |
| Excess of base (1.5 eq) in the presence of water (20 mol %/t-BUOK employed) at −50° C. | 98 | 70 | 6 |
| Base (1 eq) at −10° C. | 88 | 73 | 3 |
| Excess of base (1.5 eq) at −10° C. | 100 | 19 | — |

⇒ An excess of base: in the presence of a large excess of base (2.2 eq) at −50° C., the formation of benzyl alcohol does not take place.

⇒ The presence of water: if one of the reactants is of poor quality, it can contain a small amount of water which would induce the Cannizzaro reaction. However, at −50° C., in the presence of water (20 mol %/t-BuOK employed), scarcely 6% of benzyl alcohol is detected.

⇒ The heat level: at −10° C. in the presence of 1 equivalent of base, the formation of benzyl alcohol does not take place; on the other hand, the excess of base/heat level (−10° C.) combinat ion promotes this reaction, since the trifluoromethylation yield falls from 70 to 19%.

EXAMPLE NO. 3

ROLE OF THE NATURE OF THE SOLVENT

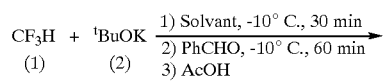

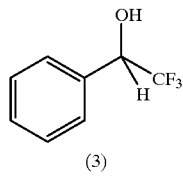

Fluoroform (3 g, 42.85 mmol) is added at −10° C. to a suitably stirred (400 r/min) solution of t-BuOK (0.53 g, 4.7 mmol) in 30 ml of anhydrous solvent (S). The reaction mixture is left stirring for 30 minutes at −10° C., before adding benzaldehyde (0.47 g, 4.4 mmol).

The solution is left stirring at −10° C. for an additional 60 minutes, before addition of acetic acid (0.5 ml).

The composition of the mixture is determined by GLC assaying with internal calibration:

| Solvent | RY (3) % |
| --- | --- |
| THF | 25 |
| DMF | 57 |
| N-Formylpiperidine | 5 |

EXAMPLE NO. 4

ROLE OF THE NATURE OF THE BASE

⇒ Associated cation (General procedure of type 2)

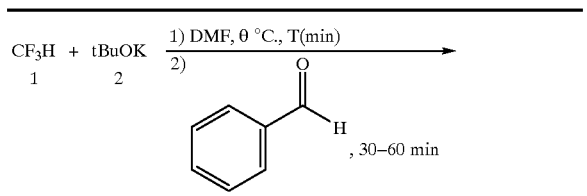

$$\text{CF}_3\text{H} + \text{PhCHO} \xrightarrow{\text{t-BuOM}} \underset{4}{\text{Ph-CH(OH)-CF}_3} + \underset{5}{\text{PhCH}_2\text{OH}}$$

| t-BuOM[a] | θ °C. | T (min) | DC (3) (%) | RY (4) (%) | YD (4) (%) | RY (5) (%) | YD (5) (%) |
|---|---|---|---|---|---|---|---|
| t-BuOK | −20 | 30 | 88 | 64 | 73 | traces | — |
| t-BuONa | −20 | 30 | 83 | 59 | 71 | traces | — |
| t-BuOLi | −20 | 30 | 32.5 | 13 | 40 | traces | — |

(a) CF$_3$H/t-BuOM/PhCOH (9/1.1/1).

⇒ Type of base (General procedure of type 1)

$$\text{CF}_3\text{H} + \underset{2}{\text{PhCHO}} \xrightarrow[\text{2) Base, θ °C.}]{\text{1) DMF, θ °C.}} \underset{4}{\text{Ph-CH(OH)-CF}_3} + \underset{5}{\text{PhCH}_2\text{OH}}$$

| Base BH | Operating Conditions 1/3/2 | θ °C. | DC (2) (%) | RY (4) (%) | RY (5) (%) |
|---|---|---|---|---|---|
| t-BuOK | 9/1.1/1 | −15° C. | 88 | 64 | 3 |
| KH (comparative) | 7.8/1.2/1 | 25° C. | 70 | 9 | 11 |
| NaH/DMSO | 9/1.3/1 | 0° C. | 94 | 50 | — |
| NaH/DMSO + 15-crown-5 | 9.3/1.3/1 + 1 eq 15-crown-5 | −10° C. | 96 | 65 | — |
| KH/DMSO | 8.7/1.15/1 | −15° C. | 91 | 66 | 3 |

EXAMPLE NO. 5

DEMONSTRATION AND ROLE OF THE TETRAHEDRAL INTERMEDIATE

1. Synthesis of Fluoral Hemiaminal and of Derivatives

Fluoroform (3 g, 42.85 mmol) is added at −10° C. to a suitably stirred solution of base in 30 ml of anhydrous DMF. This solution is kept at −10° C. for 30 min and then the following are added dropwise at the same temperature:

⇒ AcOH (0.37 g, 6.2 mmol), in the case where R═H (base: KH/DMSO, 5.7 mmol),

⇒ Me$_3$SiCl (1.3 ml, 10.25 mmol), in the case where R═Me$_3$Si (base: KHMDZ, 7 mmol)

⇒ SO$_2$ (0.8 g, 12.5 mmol), in the case where R═SO$_2$—K$^+$ (base: KH/DMSO, 5.9 mmol).

The reaction mixture is then kept at this same temperature for 30 minutes, before allowing it to rise to room temperature.

The products formed were identified by $^1$H, $^{19}$F and $^{13}$C NMR.

$$\text{CF}_3\text{H} + \text{Base} \xrightarrow[\text{2) RX}]{\text{1) DMF, −15° C., 30 min}} \underset{\text{F}_3\text{C}}{\overset{\text{OR}}{\underset{\text{H}}{|}}}\text{NMe}_2$$

RX = AcOH, (3a), R = H
RX = Me$_3$SiCl, (3b), R = Me$_3$Si
RX = SO$_2$, (3c), R = SO$_2^-$ K$^+$

| RX | RY (assayed) |
|---|---|
| AcOH | 3a, 76% |
| Me$_3$SiCl | 3b, 79% |
| SO$_2$ | 3c, 77% |

2. Synthesis of Fluoral Hydrate

Fluoroform (3 g, 42.85 mmol) is added to a suitably stirred solution, maintained at −15° C., of t-BuOK (5 mmol) in an anhydrous solvent (30 ml). After 30 min at this temperature, the reaction mixture is acidified with 2 ml of sulphuric acid.

The following table gives the results as fluoral hydrate as a function of the operating parameters:

$$\text{CF}_3\text{H} + {}^t\text{BuOK} \xrightarrow[\text{2) H}_2\text{SO}_4]{\text{1) Solvent, −15° C., 30 min}} \text{F}_3\text{C}-\text{CH(OH)}_2$$ (3)

| Solvent | RR (3)[1] % |
|---|---|
| DMF | 60 |
| N-formylpyrrolidine | 56 |
| N-formylpiperidine | 52 |

(1) $^{19}$F NMR assaying with internal standard.

EXAMPLE NO. 6

Synthesis of 2,2,2-trifluoroacetophenone

Fluoroform (3.0 g, 43 mmol) is added at −10° C. to a suitably stirred (400 r/min) solution of KHMDZ (1.15 g, 5.75 mmol) in 30 ml of anhydrous DMF. The reaction mixture is left stirring for 30 minutes at −10° C., before adding methyl benzoate (0.51 g, 3.75 mmol) dropwise.

The solution is left stirring at −10° C. for an additional 1.5 hours, before addition of acetic acid (0.6 ml).

After a conventional treatment of the reaction mixture (extraction and distillation), trifluoroacetophenone is isolated with a yield of 55%.

EXAMPLE NO. 7

1,1,1,3,3,3-Hexafluoro-2-phenyl-2-propanol

Fluoroform (3.0 g, 43 mmol) is added at −10° C. to a suitably stirred (400 r/min) solution of potassium dimsylate (5.85 mmol) in 30 ml of an anhydrous DMF/DMSO (2/1) mixture. The reaction mixture is left stirring for 30 minutes at −10° C., before adding trifluoroacetophenone (0.615 g, 3.5 mmol) dropwise.

The solution is left stirring at −10° C. for an additional 1 h 10, before addition of acetic acid (0.6 ml).

The composition of the mixture is determined by $^{19}F$ NMR and GLC assaying with internal calibration:

DC(PhCOCF$_3$)=35%

RY(PhCOH(CF$_3$)$_2$)=79%

YD(PhCOH(CF$_3$)$_2$)=44%

EXAMPLE NO. 8

Synthesis of aryl trifluoromethyl sulphide (ArSCF$_3$)

Fluoroform (3 g, 42.85 mmol) is added to a suitably stirred solution, maintained at −30° C., of ArSX (X=SAr, SO$_2$Ph, Cl, 4 mmol) in 30 ml of anhydrous DMF. A 1M solution of t-BuOK in THF (5 ml) is added dropwise to this solution and the mixture is maintained at −30° C. for 30 to 40 min, before acidification with AcOH. The composition of the mixture is determined by $^{19}F$ NMR and GLC assaying with internal standard. The products are then isolated after a conventional treatment.

The results obtained are collated in the following table:

| ArSX + CF$_3$H | | 1) DMF, -30° C.<br>2) tBuOK, -30° C., 40 min<br>3) AcOH | ArSCF$_3$ | | |
|---|---|---|---|---|---|
| (1) | | | (2) | | |
| Ar | X | | DC (1)$^{(1)}$ (%) | RY (2)$^{(2)}$ (%) | YD (2) (%) |
| Ph | SPh | | 56.5 | 77 | 136 |
| Ph | SO$_2$Ph | | 100 | 90 | 90 |
| 4-NO$_2$Ph | Cl | | 100 | 22 | 22 |

(1) GLC assaying (2) GLC and $^{19}F$ NMR assaying

EXAMPLE NO. 9

ROLE OF THE OTHER HALOFORMS

General Procedure

Approximately 5 g of potassium tert-butoxide and then 120 ml of anhydrous DMF are introduced into a completely stirred 500 ml reactor containing a mechanical stirrer (650 r/min) which is maintained under a nitrogen purge. The reaction mixture is then cooled to −40° C. by means of an acetone/dry ice bath. Approximately 5 g of benzaldehyde are then introduced dropwise, followed by 3 to 4 equivalents of haloform, by bubbling into the reaction mixture if it is gaseous (CCl$_2$FH, CF$_3$CF$_2$H), dropwise if it is liquid (CCl$_3$H). After stirring for one hour between −40 and −45° C., 5 ml of concentrated acetic acid are added dropwise and then the reaction mixture is allowed to return to room temperature. The crude reaction mixture is analysed by GLC and then by coupled GLC/MS, in order to identify the product and the by-products formed.

The reaction mixture is diluted in 150 ml of water and then the products are extracted with ethyl acetate (3×170 ml). The combined organic phases are then washed 4 to 6 times with 100 ml of water, in order to remove the DMF (GLC monitoring), and then twice with 50 ml of saturated NaCl solution. The organic phase is then dried over anhydrous MgSO$_4$ for 30 to 60 minutes and then filtered on sintered glass.

If the boiling temperature of the compound synthesized is sufficiently high, the ethyl acetate can be evaporated on a rotary evaporator under a vacuum of 20 mm Hg and at a temperature of 35° C.; in the contrary case, ethyl acetate is then distilled off at atmospheric pressure.

Fractional distillation is carried out under a vacuum of approximately 15 mm Hg. The carbinol is thus isolated with a purity of greater than 90%.

Results

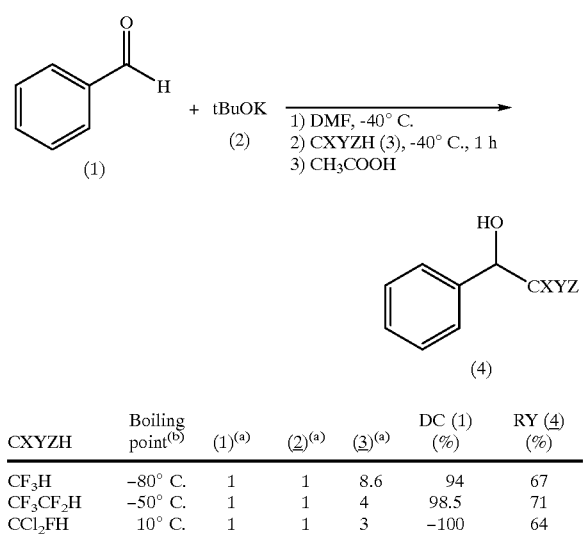

| CXYZH | Boiling point$^{(b)}$ | (1)$^{(a)}$ | (2)$^{(a)}$ | (3)$^{(a)}$ | DC (1) (%) | RY (4) (%) |
|---|---|---|---|---|---|---|
| CF$_3$H | −80° C. | 1 | 1 | 8.6 | 94 | 67 |
| CF$_3$CF$_2$H | −50° C. | 1 | 1 | 4 | 98.5 | 71 |
| CCl$_2$FH | 10° C. | 1 | 1 | 3 | −100 | 64 |

$^{(a)}$Number of equivalents
$^{(b)}$Rounded off and at atmospheric pressure

We claim:

1. A compound of formula IV:

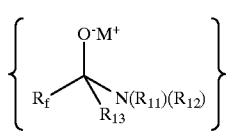

(formula IV)

wherein: M$^+$ represents a monovalent cation, and

R$_{11}$, R$_{12}$ R$_{13}$ represent an hydrocarbon chain, and R$_f$ denote CF$_3$.

2. A compound according to claim 1, wherein M$^+$ is an alkali metal or a quaternary phosphonium of at most 40 carbon atoms, and, R$_{11}$, R$_{12}$ and R$_{13}$ represent a cycloalkyl optionally connected to one another in order to form one or more rings.

* * * * *